United States Patent
Mikami et al.

[11] Patent Number: 6,017,736
[45] Date of Patent: Jan. 25, 2000

[54] METHOD OF PREPARING PURINE NUCLEOSIDE COMPOUND

[75] Inventors: Yoichi Mikami; Seiichiro Matsumoto; Shinjhi Yoshinaka; Yonosuke Sunaga; Ayumi Hasegawa, all of Tokyo, Japan

[73] Assignee: Yuki Gosei Kogyo Co., Ltd., Tokyo, Japan

[21] Appl. No.: 09/120,458

[22] Filed: Jul. 23, 1998

[30] Foreign Application Priority Data

Aug. 4, 1997 [JP] Japan ..................................... 9-209133

[51] Int. Cl.$^7$ .............................. C12P 19/40; C12P 19/38; C12P 19/00; C07H 19/16
[52] U.S. Cl. ................................. 435/88; 435/87; 435/85; 435/72; 536/27.1; 536/27.3; 536/124
[58] Field of Search .................................. 435/88, 87, 85, 435/72; 536/27.1, 27.3, 124

[56] References Cited

FOREIGN PATENT DOCUMENTS

391592A1 10/1990 European Pat. Off. .
411158A1 2/1991 European Pat. Off. .

OTHER PUBLICATIONS

Krenitsky et al, Biochemistry 20:3615–3621, 1981.
Chemical Abstracts 127(16):2196SOM, 1997.
Chemical Abstracts 118(23):232397t, 1993.
Chemical Abstracts 117(21):210765p, 1992.
Chemical Abstracts, XP–002084037, vol. 91, No. 25, p. 235, Dec. 17, 1979, abstract no. 206206.

*Primary Examiner*—Francisco Prats
*Attorney, Agent, or Firm*—Birch, Stewart, Kolasch & Birch, LLP

[57] ABSTRACT

The present invention provides a method of preparing stably and at a high yield a purine nucleoside compound by utilizing an exchange reaction of a nucleic acid base which is carried out in the presence of an enzyme, and also provides a microorganism capable of producing uracil thymine dehydrogenase or dihydrouracil dehydrogenase. In preparing the purine nucleoside compound, a pyrimidine nucleoside compound and a purine base are subjected to a base exchange reaction in an aqueous solution containing phosphate ions in the presence of pyrimidine nucleoside phosphorylase and purine nucleoside phosphorylase. The pyrimidine base formed by the base exchange reaction is converted by a microorganism or an enzyme derived from the microorganism into a compound incapable of acting as substrates of pyrimidine nucleoside phosphorylase and purine nucleoside phosphorylase so as to obtain a desired product of purine nucleoside compound.

6 Claims, 1 Drawing Sheet

METHOD OF PREPARING PURINE NUCLEOSIDE COMPOUND

BACKGROUND OF THE INVENTION

The present invention relates to a method of preparing a purine nucleoside compound at a high yield by utilizing an exchange reaction of nucleic acid base, which is carried out in the presence of an enzyme, and to microorganisms producing enzymes used for the preparation of the purine nucleoside compound.

Known is a method of preparing a nucleoside compound by utilizing an exchange reaction of nucleic acid base carried out in the presence of an enzyme. In the known method, however, equilibrium takes place between the starting materials and the reaction products, resulting in failure to improve the yield. For overcoming the difficulty, Japanese Patent Disclosure (Kokai) No. 4-197193 disclosed an exchange reaction of a base between inosine or 2'-deoxyinosine (hereinafter referred to as "deoxyinosine") and pyrimidine base, which is carried out in an aqueous solution of a phosphate in the presence of purine nucleoside phosphorylase (EC2.4.2.1) and pyrimidine nucleoside phosphorylase (EC2.4.2.2), and then hypoxanthine formed by the exchange reaction is converted into uric acid by xanthine oxidase so as to improve the reaction yield. In this method, since uric acid cannot act as a substrate of nucleoside phosphorylase, the reaction proceeds unidirectionally to form pyrimidine nucleoside.

However, JP 4-197193 noted above, which is directed to a method of efficiently preparing pyrimidine nucleoside by using inosine or deoxyinosine and pyrimidine base as starting materials, does not disclose a method of preparing a purine nucleoside compound by using a pyrimidine nucleoside compound and a purine base as starting materials which are readily available at low cost. Where a pyrimidine nucleoside compound is used as a starting material, it is necessary to add an enzyme serving to decompose the pyrimidine base formed by the base exchange reaction to the reaction system in order to deviate the equilibrium and to improve the reaction yield. However, preparation or isolation of the enzyme from natural product in a high activity state has not yet been reported. In other words, a method of preparing at a high yield a purine nucleoside compound using pyrimidine nucleoside compound as a starting material has not yet been established. Naturally, it is of high importance to develop a method of preparing a purine nucleoside compound stably at a high yield.

BRIEF SUMMARY OF THE INVENTION

Under the circumstances, the present inventors have conducted an extensive research on microorganisms producing enzymes effective for converting pyrimidine base obtained in the exchange reaction between a pyrimidine nucleoside compound and purine base into a compound incapable of acting as substrates of pyrimidine nucleoside phosphorylase and purine nucleoside phosphorylase, and found that microorganisms belonging to Arthrobactor species, Bacillus species, Pseudomonas species, or Rhodococcus species are capable of producing the such enzymes, arriving at the present invention.

According to an aspect of the present invention, there is provided a method of preparing a purine nucleoside compound at a high yield, comprising the step of subjecting a pyrimidine nucleoside compound and a purine base to a base exchange reaction in an aqueous solution containing phosphate ions in the presence of purine nucleoside phosphorylase and pyrimidine nucleoside phosphorylase, wherein pyrimidine base formed by the reaction is converted by a microorganism or an enzyme derived from the microorganism into a compound incapable of acting as substrates of pyrimidine nucleoside phosphorylase and purine nucleoside phosphorylase.

According to another aspect of the present invention, there is provided a microorganism capable of producing uracil thymine dehydrogenase or dihydrouracil dehydrogenase, the microorganism being selected from the group consisting of Arthrobacter species YGK 222 (FERM BP-5907), *Bacillus megaterium* YGK 252 (FERM BP-5908), and Pseudomonas species YGK 443 (FERM BP-5909).

The method of the present invention for preparing a purine nucleoside compound by utilizing an exchange reaction of a nucleic acid base makes it possible to prepare a purine nucleoside compound at a high yield and with a high stability using as starting materials a pyrimidine nucleoside compound and a purine base which are readily available at a low cost.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
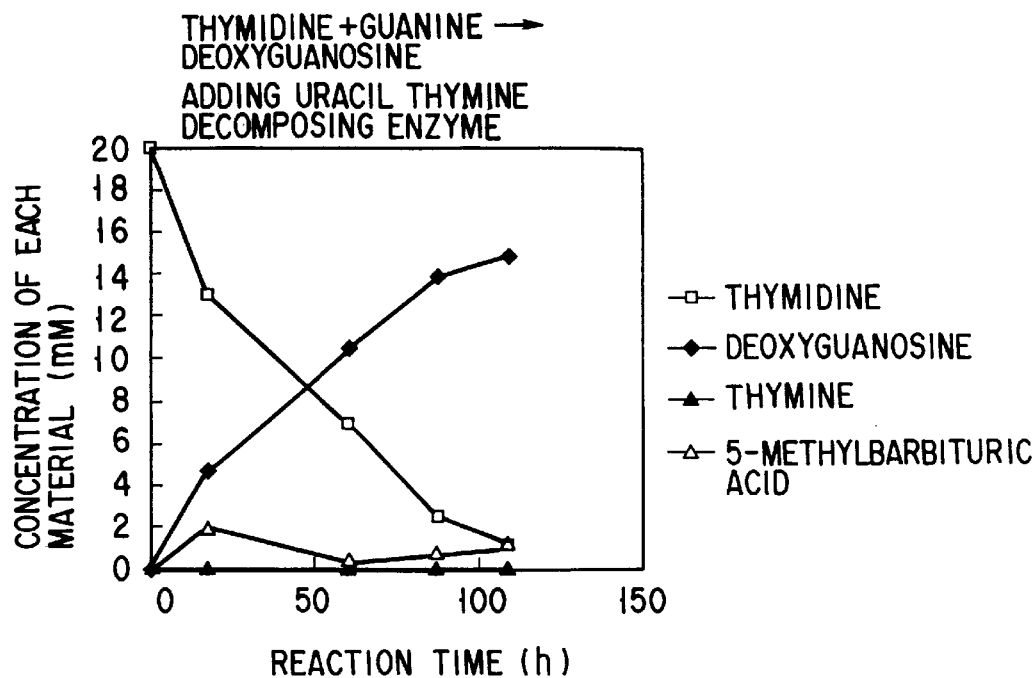
FIG. 1 is a graph showing changes with time in the concentration of each of the components of the reaction system in Example 1 containing an uracil thymine decomposing enzyme solution.

A first aspect of the present intention is directed to a method of preparing a purine nucleoside compound, comprising the step of subjecting a pyrimidine nucleoside compound and a purine base to a base exchange reaction in an aqueous solution containing phosphate ions in the presence of purine nucleoside phosphorylase and pyrimidine nucleoside phosphorylase, wherein pyrimidine base formed by the reaction is converted by a microorganism or an enzyme derived from the microorganism into a compound incapable of acting as substrates of pyrimidine nucleoside phosphorylase and purine nucleoside phosphorylase.

<Starting Materials>

The pyrimidine nucleoside compound used as a starting material is either of natural type or nonnatural type and is not particularly limited as far as the compound accepts the action of pyrimidine nucleoside phosphorylase and the formed pyrimidine base accepts the action of the decomposing enzyme used. For example, the pyrimidine nucleoside compound includes uridine, deoxyuridine, 5-methyl uridine, and thymidine, and also possible to use a nonnatural type pyrimidine nucleoside and nonnatural deoxypyrimidine nucleoside.

The purine base used in the present invention is not particularly limited as far as the base accepts the action of purine nucleoside phosphorylase and includes, for example, natural purine bases such as adenine, guanine, and hypoxanthine; and nonnatural purines including benzimidazole; aminated purines such as 2-aminopurine, and 2,6-diaminopurine; halogenated purines such as 2-chloropurine, 6-chloropurine, 2,6-dichloropurine and 2-amino-6-chloropurine; and thionated purines such as 6-mercptopurine, 6-methyl thiopurine.

<Microorganisms and Enzymes>

In principle, the purine nucleoside phosphorylase and pyrimidine nucleoside phosphorylase used in the present invention may be of any origin.

The enzymes derived from microorganisms, which are used in the present invention for decomposing pyrimidine base, are not particularly limited, as far as these enzymes permit converting the pyrimidine base formed by the base exchange reaction into a compound incapable of acting as substrates of pyrimidine nucleoside phosphorylase and purine nucleoside phosphorylase, and include, for example, uracil thymine dehydrogenase (EC1.2.99.1) and dihydrouracil dehydrogenase (EC1.3.1.1). Particularly, it is desirable to use enzymes produced from the microorganisms specified herein later, and from *Rhodococcus erythropolis* JCM 3132 or *Rhodococcus erythropolis* JCM 3191.

As used herein, "by a microorganisms or enzymes derived from the microorganisms" means carrying out in a decomposition reaction of pyrimidine base by using a suspension of the microorganisms (i.e. bacteria suspension), or enzymes produced from the microorganisms.

Accordingly, in the present invention, a suspension containing microorganisms, or enzymes produced from the microorganisms may be used for the decomposition reaction of pyrimidine base. In other words, the bacteria suspension itself containing microorganisms may be used for the decomposition reaction of pyrimidine base. Alternatively, the enzymes produced from the suspended microorganisms may be used for the decomposition reaction of pyrimidine base.

<Stabilizer of ribose 1-phosphate>

In the base exchange reaction of the present invention, which is carried out in the presence of pyrimidine nucleoside phosphorylase and purine nucleoside phosphorylase, sugar derivatives of ribose 1-phosphate or deoxyribose 1-phosphate are produced as intermediates. These intermediates are unstable. If left to stand, these intermediates are decomposed with time into a sugar such as ribose or deoxyribose and phosphate ions. If phosphatase is present in the reaction system, the hydrolysis of the intermediates is further accelerated. It should be noted that a sugar such as ribose or deoxyribose formed by decomposition of the intermediate does not acting a substrate of nucleoside phosphorylase, leading to decreased formation of purine nucleoside or deoxypurine nucleoside. In order to improve the forming efficiency of these purine nucleoside compounds, the present inventors have conducted an extensive research in an attempt to find a substance effective for stabilizing a sugar derivative such as ribose 1-phosphate or deoxyribose 1-phosphate and also effective for inhibiting the activity of phosphatase, finding that a combination of some kinds of complex-forming compounds is effective for stabilizing the sugar derivative and for inhibiting the activity of phosphatase.

Specifically, the present inventors have found that it is effective to use at least one compound selected from the group consisting of glycine, iminodiacetic acid, nitrilotriacetic acid, ethylenediaminetetraacetic acid (EDTA), ethylene glycol (2-aminoethylether)tetraacetic acid (EGTA) and salts thereof in combination with boric acid or its salt. Particularly, a prominent effect is produced by the combination of boric acid and ethylenediaminetetraacetic acid.

<Reacting Conditions and Isolation-Refining>

Concerning the reacting conditions, the initial concentration of the pyrimidine nucleoside compound used as a starting material in the present invention should be 5 to 300 mM, preferably 10 to 50 mM. On the other hand, the initial concentration of the purine base, which is generally low in solubility, should be 5 to 300 mM, preferably 10 to 50 mM, where all the purine base added initially is assumed to be dissolved. It suffices for the initial concentration of the phosphate ions to be 1 to 20 mM. In general, the nucleoside and purine base are set at the same initial concentration. Also, the yield of the product purine nucleoside compound is increased in general with increase in the ratio in concentration of the nucleoside to the phosphate ions.

When it comes to the complex-forming compounds used as a stabilizer, the amount of boric acid or its salt should be 5 to 200 mM, preferably 50 to 100 mM. On the other hand, the amount of the counterpart of the combination, e.g., EDTA or its salt, should be 2 to 12 mM, preferably 4 to 6 mM.

The pH value of the reacting system should be 6.5 to 10.5, preferably 7.0 to 8.0. The reaction temperature should be 35 to 60° C., preferably 35 to 45° C.

The formed product can be isolated from the reaction mixture by means of, for example, crystallization or chromatography.

<Principle and Theory of the Present Invention>

1. In the first stage of the present invention, a reaction between a pyrimidine nucleoside compound and phosphate ion is carried out in the presence of phosphate ion and pyrimidine nucleoside phosphorylase to form pyrimidine base and a sugar derivative in which the phosphate ion is bonded to 1-position of a sugar such as ribose 1-phosphate or 2-deoxyribose 1-phosphate.

2. In the second stage, a substitution reaction is carried out between the sugar derivative formed in the first stage and the purine base in the presence of purine nucleoside phosphorylase so as to form a purine nucleoside compound and phosphate ion.

Arranging the stage 1 and 2, a base exchange reaction is carried out between the pyrimidine nucleoside and the purine base in the first and second stages in the presence of purine nucleoside phosphorylase and pyrimidine nucleoside phosphorylase so as to form a pyrimidine base and a purine nucleoside compound.

3. In the present invention, the reaction system contains an enzyme serving to convert the pyrimidine base into a compound incapable of acting as substrates of pyrimidine nucleoside phosphorylase and purine nucleoside phosphorylase. Alternatively, the reaction system contains microorganisms producing the particular enzyme. It is desirable to use in the present invention microorganisms producing an enzyme such as uracil thymine dehydrogenase or dihydrouracil dehydrogenase, though the microorganisms used in the present invention are not particularly limited.

In the present invention, the particular enzyme or microorganisms producing the enzyme is present in the reaction system together with an electron acceptor so as to convert the pyrimidine base into a compound incapable of acting as substrates of pyrimidine nucleoside phosphorylase and purine nucleoside phosphorylase. Incidentally, where a bacteria suspension is used in the reaction, an electron acceptor need not be added to the reaction system because the electron acceptor is contained in the bacteria. It should be noted that the converted pyrimidine base, which is incapable of acting as substrates of purine nucleoside phosphorylase and pyrimidine nucleoside phosphorylase, is not involved in the substrate exchange reaction and, thus, is excluded from the reaction system. As a result, the equilibrium of reaction is shifted toward a side on which the product purine nucleoside compound is formed, making it possible to obtain the desired product at a high yield.

4. Further, it is possible for the reaction system to contain an enzyme serving to further decompose the converted compound, if necessary, as described below in conjunction with a preferred embodiment.

<Preferred Embodiment>

In a preferred embodiment of the present invention, uridine or 2'-deoxyuridine (hereinafter referred to as "deoxyuridine") is used as a starting material of a pyrimidine nucleoside compound. A purine base is used as a nucleic acid base. Further, purine nucleoside phosphorylase, pyrimidine nucleoside phosphorylase and uracil thymine dehydrogenase (EC 1.2.99.1) are used as enzymes.

(1) In the first stage, a reaction between uridine or deoxyuridine and phosphate ions is carried out in the presence of phosphate ions and pyrimidine nucleoside phosphorylase so as to form uracil and ribose 1-phosphate or 2-deoxyribose 1-phosphate (hereinafter referred to as "deoxyribose 1-phosphate").

(2) In the second stage, a substitution reaction between the formed ribose 1-phosphate or deoxyribose 1-phosphate and the purine base is carried out in the presence of purine nucleoside phosphorylase. Purine nucleoside and phosphate ions are formed by the reaction between ribose 1-phosphate and the purine base. On the other hand, 2'-deoxypurine nucleoside (hereinafter referred to as "deoxypurine nucleoside") and phosphate ions are formed by the reaction between deoxyribose 1-phosphate and the purine base.

In other words, in the first and second stages described above, base exchange reactions are carried out between uridine or deoxyuridine and the purine base in the presence of purine nucleoside phosphorylase and pyrimidine nucleoside phosphorylase so as to form uracil and purine nucleoside or deoxypurine nucleoside.

(3) By allowing uracil thymine dehydrogenase alone or both uracil thymine dehydrogenase and an electron acceptor (oxidation type) such as NAD to be present in the reaction system, uracil formed by the decomposition of uridine or deoxyuridine is irreversibly converted into barbituric acid. Since the formed barbituric acid cannot act as substrates of purine nucleoside phosphorylase and pyrimidine nucleoside phosphorylase, barbituric acid is not involved in the exchange reaction and is excluded from the reaction system. As a result, the equilibrium of reaction is shifted toward a side on which the desired product of purine nucleoside compound is formed, making it possible to obtain the desired product at a high yield.

(4) Further, by allowing barbiturase (EC 3.5.2.1) to be present in the reaction system, barbituric acid is decomposed into urea and malonic acid. As a result, the exchange reaction carried out in the presence of uracil thymine dehydrogenase is promoted.

For example, where 2'-deoxyguanosine (herein after referred to as "deoxyguanosine") is obtained as a product purine nucleoside compound from the starting materials of deoxyuridine as a pyrimidine nucleoside compound and guanine as a purine base, the reactions are carried out as follows:

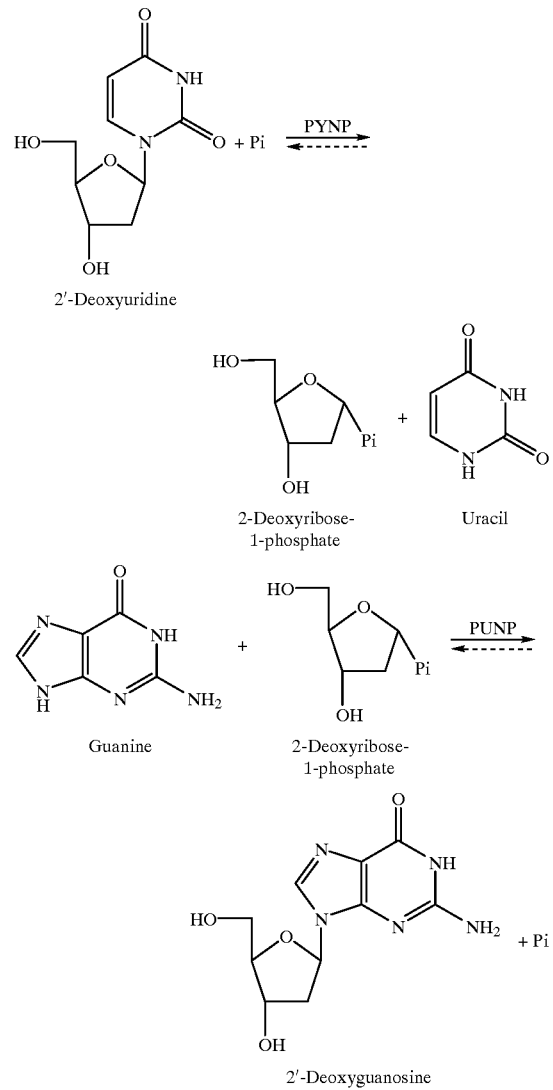

In the reaction formula given above, the abbreviations PYNP, PUNP and Pi represent pyrimidine nucleoside phosphorylase, purine nucleoside phosphorylase and phosphate ions, respectively.

From the first and second stages (1) and (2) described previously, the reaction formula given below is established:

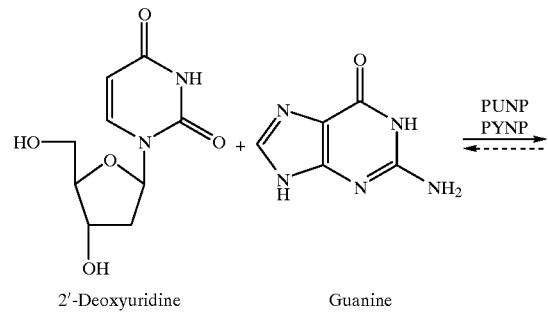

-continued

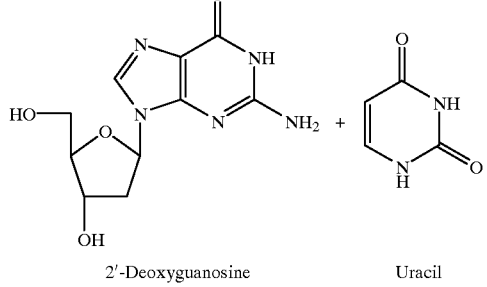

2′-Deoxyguanosine      Uracil

In the reaction formula given above, the abbreviations PYNP and PUNP represent pyrimidine nucleoside phosphorylase and purine nucleoside phosphorylase, respectively, as in the reaction formula described previously.

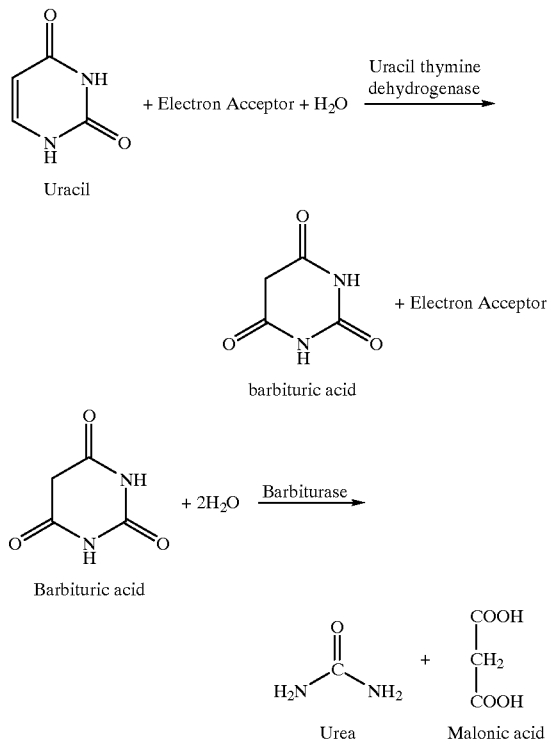

In a preferred embodiment of the present invention, uridine or deoxyuridine is used as a pyrimidine nucleoside compound. Also, a purine base is used as a nucleic acid base. Further, purine nucleoside phosphorylase, pyrimidine nucleoside phosphorylase and dihydrouracil dehydrogenase (EC 1.3.1.1) are used as enzymes.

(1) Reaction between uridine or deoxyuridine and phosphate ions is carried out in the presence of pyrimidine nucleoside phosphorylase to form uracil and ribose 1-phosphate or deoxyribose 1-phosphate.

(2) Then, ribose 1-phosphate or deoxyribose 1-phosphate thus formed is subjected to a substitution reaction with a purine base in the presence of purine nucleoside phosphorylase. In this case, purine nucleoside and phosphate ions are formed by the reaction between ribose 1-phosphate and the purine base. Likewise, deoxypurine nucleoside and phosphate ions are formed by the reaction between deoxyribose 1-phosphate and the purine base.

Where reactions (1) and (2) given above are taken together, it can be said that base exchange reactions are carried out between uridine or deoxyuridine and a purine base in the presence of purine nucleoside phosphorylase and pyrimidine nucleoside phosphorylase to form purine nucleoside or deoxypurine nucleoside and uracil.

(3) By allowing dihydrouracil dehydrogenase alone or both dihydrouracil dehydrogenase and an electron acceptor (reduction type) such as NADH to be present in the reaction system, the uracil formed by decomposition of uridine or deoxyuridine is irreversibly converted into dihydrouracil. The dihydrouracil thus formed, which cannot act as substrates of purine nucleoside phosphorylase and pyrimidine nucleoside phosphorylase, is not involved in the exchange reaction of the substrate and, thus, excluded from the reaction system. As a result, the equilibrium of reaction is shifted toward a side on which the desired product of purine nucleoside compound is formed, making it possible to obtain the desired product quantitatively.

(4) Further, dihydrouracil is decomposed into N-carbamoyl-β-alanine by the presence of dihydropyrimidinase (EC 3.5.2.2). As a result, the reaction of dihydrouracil dehydrogenase is promoted.

Where, for example, 2′-deoxyadenosine (hereinafter referred to as "deoxyadenosine") is obtained as a desired purine nucleoside compound from deoxyuridine, which is a pyrimidine nucleoside compound used as one of the starting materials, and adenine, which is a purine base used as the other starting material, the reactions are carried out as follows:

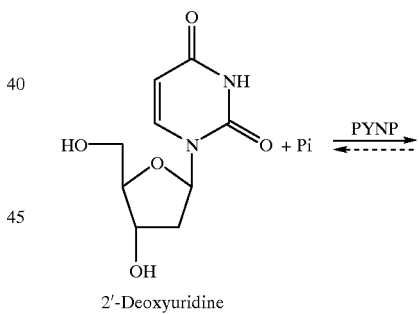

2′-Deoxyuridine

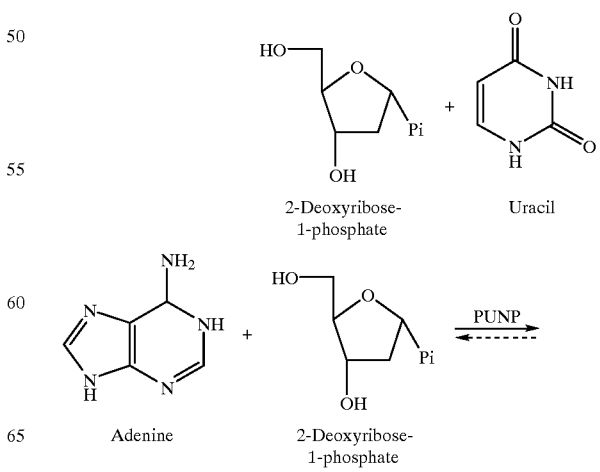

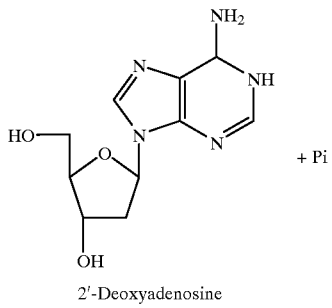

2'-Deoxyadenosine

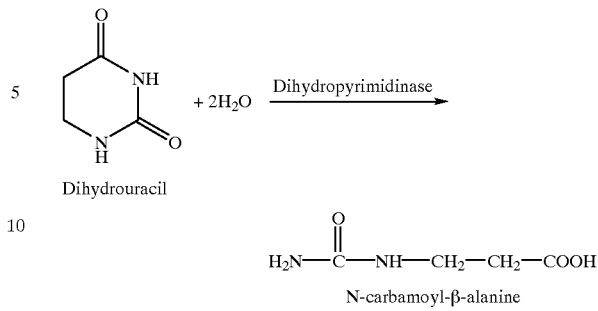

N-carbamoyl-β-alanine

The abbreviations PYNP, PUNP and Pi given in the above reaction formula are as defined previously.

The reaction formula given below is established from items (1) and (2) above:

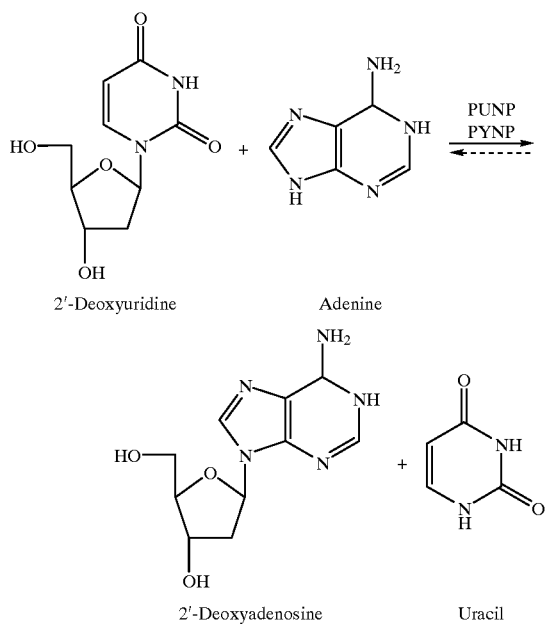

2'-Deoxyuridine     Adenine

2'-Deoxyadenosine     Uracil

The abbreviations PYNP and PUNP given in the above reaction formula are as defined previously.

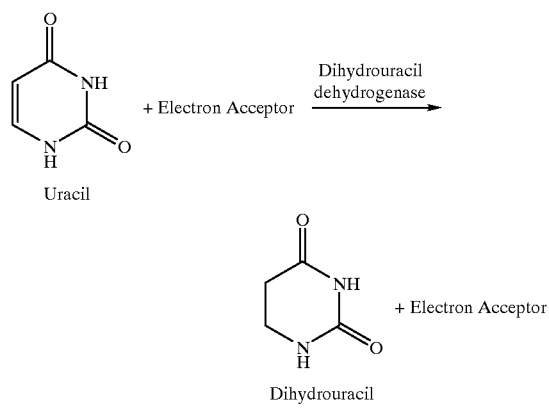

Uracil

Dihydrouracil

The second aspect of the present invention is directed to microorganisms producing uracil thymine dehydrogenase or dihydrouracil dehydrogenase. These microorganisms are selected from the group consisting of Arthrobactor species YGK 222 (FERM BP-5907), Bacillus megaterium YGK 252 (FERM BP-5908), and Pseudomonas species YGK 443 (RERM BP-5909).

<Enzyme-producing Microorganisms and Identification thereof>

The present inventors have found that at least one of a series of enzymes serving to convert pyrimidine base into compounds incapable of acting as substrates of pyrimidine nucleoside phosphorylase and purine nucleoside phosphorylase are produced by microorganisms. Specifically, these microorganisms have been found to produce at least one enzyme selected from the group consisting of (1) uracil thymine dehydrogenase, (2) dihydrouracil dehydrogenase, (3) uracil thymine dehydrogenase and barbiturase (EC3.5.2.1) and (4) dihydrouracil dehydrogenase and dihydropyrimidinase (EC3.5.2.2).

<Culturing Conditions and Preparation of Enzymes>

These microorganisms grow well in the ordinary culture medium of bacteria and produce the desired enzymes. For enhancing the enzyme activity, it is effective to add pyrimidine base to the culture medium.

The cultured strain can be used as it is as a crude enzyme. It is also possible to obtain a crude enzyme by the ordinary method for use in the present invention.

Arthrobactor species YGK 222 (FERM BP-5907)
Bacillus megaterium YGK 252 (FERM BP-5908)
Pseudomonas species YGK 443 (FERM BP-5909)
Rhodococcus erythropolis JCM 3132
Rhodococcus erythropolis JCM 3191

The symbol "JCM" denotes that the strains are preserved in Japan Collection of Microorganisms in The Institute of Physical and Chemical Research (Rikagaku Kenkyusho). These strains are available from Japan Collection of Microorganisms noted above. The other strains, i.e., YGK 222 (FERM BP-5907), YGK 252 (FERM BP-5908), YGK 443 (FERM BP-5909), are deposited in National Institute of Bioscience and Human-Technology, Agency of Industrial Science and Technology. These microorganisms YGK 222 (FERM BP-5907), YGK 252 (FERM BP-5908), YGK 443 (FERM BP-5909) were deposited on Apr. 11, 1997 pursuant to BUDAPEST TREATY ON THE INTERNATIONAL RECOGNITION OF THE DEPOSIT OF MICROORGANISMS FOR THE PURPOSES OF PATENT PROCEDURE. These microorganisms are deposited under the deposition numbers put in the parentheses.

The bacterial properties of these deposited strains were studied in accordance with "Bergey's Manual of Determinative Bacteriology No. 8 (1975)", "Bergey's Manual of Systematic Bacteriology No. 1 (1984) and No. 2 (1986)" to obtain the results given below. The experiments were carried out by the method described in "Classification and Identification of Microorganisms, compiled by Takeji Hasegawa, revised edition, published by Gakkai Shuppan Center, 1985". These references are incorporated herein by reference.

Arthrobacter species YGK 222:
1. Morphological Properties
   (1) Size of the cell: rod sized at 0.5 to 0.7×1.0 to 5.0 μm
   (2) Gram's strain: positive
   (3) Polymorphism of cell: Recognized is a prominent polymorphism of coccus to rod accompanying the growth cycle.
   (4) Motility: Motility is recognized in the culturing for 5 to 24 hours in a liquid culture medium prepared by adding bouillon to yeast extract.
   (5) Adherent state of flagellum: 1 to 2 side flagella
   (6) Spore: None
   (7) Acid-fastness: None
2. Culturing Properties
   (1) Bouillon agar plate culturing:
   A circular wavy colony, which is milk white, translucent and has a rough surface, is formed in the culturing at 30° C. for 24 hours.
   (2) Bouillon agar slant culturing:
   Pale yellow and translucent microorganisms grow well over the entire culture medium.
   (3) Bouillon liquid culturing:
   Growing rate is low. A good growth is observed in a shake culture having yeast extract added thereto.
   (4) Bouillon gelatin stab culture: The surface region alone is slightly liquefied.
   (5) Litmus milk: No change
3. Physiological Properties
   (1) Reduction of nitrate: negative
   (2) Denitrification reaction: negative
   (3) MR test: negative
   (4) VP test: negative
   (5) Indole formation: negative
   (6) Hydrogen sulfide formation: negative
   (7) Utilization of citric acid:
   Christensen agar: negative
   Koser medium: negative
   (8) Utilization of inorganic nitrogen source
   Nitrate: positive
   Ammonium salt: negative
   (9) Chromogenesis: none
   (10) Urease: negative
   (11) Oxidase: negative
   (12) Catalase: positive
   (13) Range of growth
   pH range: 5.5 to 9.5
   Temperature range: 19 to 38° C.
   (14) Relation to free oxygen: aerobic
   (15) O—F test
   Glucose: no change
   Saccharose: no change
   (16) Utilization of various carbon sources
   L-arabinose ±
   D-xylose +
   D-glucose +
   D-mannose +
   D-fructose +
   D-galactose +
   Maltose +
   Sucrose +
   Lactose −
   Trehalose +
   D-sorbitol +
   D-mannitol +
   Inositol +
   Glycerin −
   Starch −
4. GC content (by HPLC method):
   G+C (mol %)=69.6
   The microorganism has been clarified to belong to Arthrobactor species based on the bacteriological properties given above.

*Bacillus megaterium* YGK 252
1. Morphological properties
   (1) Size of the cell: rod sized at 1.6×4.0 to 9.0 μm
   (2) Gram's strain: positive
   (3) Polymorphism of cell: None
   (4) Motility: Recognized
   (5) Adherent state of flagellum: Recognized. *Peritrichal flagella*
   (6) Spore: Sporangia are not swollen. The spore is ellipsoidal.
   (7) Acid-fastness: None
2. Culturing Properties
   (1) Bouillon agar plate culturing:
   A circular wavy colony, which is milk white, opaque and has a rough surface, is formed in the culturing at 30° C. for 24 hours.
   (2) Bouillon agar slant culturing:
   Pale yellow and opaque microorganisms, having a slightly dry surface and a rough periphery, grow well along a stroke.
   (3) Bouillon liquid culturing:
   Growing rate is low. A good growth is observed if yeast extract is added.
   (4) Bouillon gelatin stab culture: The surface region alone is slightly liquefied.
   (5) Litmus milk: Slightly acidic and coagulation is observed.
3. Physiological Properties
   (1) Reduction of nitrate: positive
   (2) Denitrification reaction: positive
   (3) MR test: positive
   (4) VP test: negative
   (5) Indole formation: negative
   (6) Hydrogen sulfide formation: negative
   (7) Utilization of citric acid:
   Christensen agar: positive
   Koser medium: positive
   (8) Utilization of inorganic nitrogen source
   Nitrate: positive
   Ammonium salt: positive
   (9) Chromogenesis: none
   (10) Urease: positive
   (11) Oxidase: positive
   (12) Catalase: positive
   (13) Range of growth
   pH range: 5.5 to 10.5
   Temperature range: 10 to 43° C.
   (14) Relation to free oxygen: aerobic
   (15) O—F test
   Glucose: no change
   Saccharose: no change

(16) Utilization of various carbon sources
L-arabinose –
D-xylose –
D-glucose –
D-mannose –
D-fructose –
D-galactose –
Maltose –
Sucrose –
Lactose –
Trehalose –
D-sorbitol –
D-mannitol –
Inositol –
Glycerin –
Starch +
4. GC content (by HPLC method):
G+C (mol %)=34.7

The microorganism has been clarified to belong to *Bacillus megaterium* based on the bacteriological properties given above.

Pseudomonas species YGK 443
1. Morphological properties
   (1) Size of the cell: rod sized at 0.4 to 0.6×0.6 to 2.4 µm
   (2) Gram's strain: negative
   (3) Polymorphism of cell: None
   (4) Motility: Recognized
   (5) Adherent state of flagellum: 4 to 5 polar flagella were observed.
   (6) Spore: None
   (7) Acid-fastness: negative
2. Culturing Properties
   (1) Bouillon agar plate culturing:
   A circular wavy colony, which is milk white, translucent and has a smooth surface, is formed in the culturing at 30° C. for 24 hours.
   (2) Bouillon agar slant culturing:
   Pale yellow, translucent and lustrous microorganisms grow well along a stroke.
   (3) Bouillon liquid culturing: A good growth is observed in a shaking culture.
   (4) Bouillon gelatin stab culture: No change.
   (5) Litmus milk: Alkaline and not peptonized.
3. Physiological Properties
   (1) Reduction of nitrate: positive
   (2) Denitrification reaction: negative
   (3) MR test: negative
   (4) VP test: negative
   (5) Indole formation: negative
   (6) Hydrogen sulfide formation: negative
   (7) Utilization of citric acid:
   Christensen agar: positive
   Koser medium: positive
   (8) Utilization of inorganic nitrogen source
   Nitrate: positive
   Ammonium salt: positive
   (9) Fluorescent chromogenesis: none
   (10) Urease: positive
   (11) Oxidase: positive
   (12) Catalase: positive
   (13) Range of growth
   pH range: 4.2 to 10.5
   Temperature range: 17 to 43° C.
   (14) Relation to free oxygen: aerobic
   (15) O—F test
   Glucose: O (oxidative)
   Saccharose: no change
   (16) Decomposition of arginine: negative
   (17) Utilization of various carbon sources
   L-arabinose +
   D-xylose +
   D-glucose +
   D-mannose +
   D-fructose +
   D-galactose +
   Maltose +
   Sucrose +
   Lactose –
   Trehalose +
   D-sorbitol –
   D-mannitol +
   Inositol +
   Glycerin +
   Starch –
4. GC content (by HPLC method):
G+C (mol %)=62.3

The microorganism has been clarified to belong to Pseudomonas species based on the bacteriological properties given above.

EXAMPLES:

The present invention is described more in detail with reference to Preparation Examples, Experiments and Examples which follow.

Preparation Example 1

Preparation of a Bacteria Suspension Containing Purine Nucleoside Phosphorylase and Pyrimidine Nucleoside Phosphorylase

*Bacillus stearothermophilus* JTS 859 (FERM P-9666), which is a bacteria producing purine nucleoside phosphorylase (PUNP) and pyrimidine nucleoside phosphorylase (PYNP), was cultured as follows.

Used for the culturing of the bacteria was a culture medium having a pH value of 6.2 and consisting of 10 g of bactotryptone, 5 g of yeast extract, 3 g of glucose, 3 g of table salt, 1 g of inosine and 1 L(liter) of water. Added to 1.5 L of the culture medium was 3×10$^7$ spores of *Bacillus stearothermophilus* JTS 859 (FERM P-9666) for culturing at an air circulation of 1 vvm, a culturing temperature of 65° C. and a pH value of 6.0 to 6.4 using an 3 L volume of a jar fermenter equipped with upper and lower stirring vanes each having a diameter of 70 mm. During the culture, the stirring vanes were rotated at 500 rpm. After completion of the culturing, the bacteria was centrifugally collected (10,000 G, 4° C., 15 minutes). 20 g of wet bacteria thus obtained was suspended in 30 mL (milliliters) of 10 mM potassium phosphate solution (pH 7) so as to prepare a bacteria suspension containing purine nucleoside phosphorylase and pyrimidine nucleoside phosphorylase (hereinafter referred to as "PUNP·PYNP enzyme solution").

Preparation Example 2

Preparation of Bacteria Suspension Having Uracil and Thymine Decomposing Activity A bacteria suspension of Arthrobactor species YGK 222 (FERM BP-5907), *Bacillus megaterium* YGK 252 (FERM BP-5908), Pseudomonas species YGK 443 (FERM BP-5909), *Rhodococcus erythropolis* JCM 3132 or *Rhodococcus erythropolis* JCM 3191, each having uracil and thymine decomposing activity, was prepared as follows.

Used for the culturing of the bacteria was a culture medium having a pH value of 7.0 and consisting of 2 g of uracil, 1 g of potassium dihydrogenphosphate, 3 g of dipotassium hydrogenphosphate, 6 g of yeast extract and 1 L of water. The culture medium was put in a 2 L volume of an Erlenmeyer flask and inoculated with $3 \times 10^7$ bacteria or spores of the microorganisms noted above. Under this condition, culturing was performed for 15 hours at 35° C while rotating the Erlenmeyer flask at 200 rpm.

After completion of the culturing, the bacteria was centrifugally collected (10,000 G, 4° C., 15 minutes), and the wet bacteria thus obtained was suspended in 6 mL of a buffer solution (pH 7) containing 10 mM of potassium phosphate so as to prepare a bacteria suspension (hereinafter referred to as "uracil-thymine decomposing enzyme solution").

Experiment 1
Production of Uracil and Thymine Decomposing Enzyme from Microorganisms One milliliter of reaction solution containing either 50 mM of uracil or 50 mM of thymine, 100 mM of phosphate buffer solution (pH 7), and 0.05 mL of any one of the uracil-thymine decomposing enzyme solutions derived from the strains prepared in Preparation Example 2 was allowed to react at 35° C for 15 minutes, and the uracil and thymine decomposing activity in the reaction solution was measured by a High Performance Liquid Chromatography. Table 1 shows the results.

The decomposing activity U shown in Table 1 denotes the amount of the enzyme activity required for decomposing 1 μmol of the substrate (uracil or thymine) per minute at 35° C.

TABLE 1

| Strain | Decomposing activity (U/wet bacteria g) | |
|---|---|---|
| | Uracil | Thymine |
| Arthrobacter species YGK 222 | 36.4 | 14.5 |
| Bacillus megaterium YGK 252 | 5.8 | 2.1 |
| Pseudomonas species YGK 443 | 2.2 | 1.4 |
| Rhodococcus erythropolis JCM 3132 | 10.6 | 4.2 |
| Rhodococcus erythropolis JCM 3191 | 7.8 | 3.2 |

Experiment 2
Producing Enzyme of Uracil-Thymine Decomposing Enzyme-Producing Bacteria One milliliter of reaction solution containing 50 mM of uracil, 100 mM of phosphate solution (pH 7) and 0.05 mL of any one of the uracil-thymine decomposing enzyme solutions derived from the strains prepared in Preparation Example 2 was allowed to react at 35° C for 15 to 30 minutes. The presence of uracil thymine dehydrogenase, barbiturase, dihydrouracil dehydrogenase and dihydropyrimidinase as well as formation and disappearance of barbituric acid and dihydrouracil was detected by tracing with a High Performance Liquid Chromatography. Table 2 shows the results. The symbols "+" and "−" in Table 2 denote that the enzyme was detected and not detected, respectively.

It should be noted that where, for example, the activity of dihydropyrimidinase is higher than that of dihydrouracil dehydrogenase, the formed product of dihydrouracil is not detected. It follows that the symbol "−" in Table 2 does not necessarily deny by 100% the presence of the particular enzyme.

TABLE 2

| | Detection of Each Enzyme | | | |
|---|---|---|---|---|
| Strain No. | Uracil thymine dehydrogenase | Barbiturase | Dihydrouracil dehydrogenase | Dihydropyrimidinase |
| YGK 222 | + | + | − | − |
| YGK 443 | + | + | + | + |
| YGK 252 | + | + | + | + |
| JCM 3132 | + | + | − | − |
| JCM 3191 | + | + | − | − |

Example 1
Preparation of Purine Nucleoside by Using PUNP-PYNP Enzyme Solution and Uracil-Thymine Decomposing Enzyme Solution 100 mL of an aqueous solution (pH 7) containing 20 mM of thymidine, 20 mM of guanine, 1.25 mM of potassium phosphate, 2 mL of PUNP-PYNP enzyme solution prepared in Preparation Example 1, 0.5 mL of uracil-thymine decomposing enzyme solution derived from Arthrobactor species YGK 222, which was prepared in Preparation Example 2, 100 mM of boric acid, and 4 mM of ethylenediaminetetraacetatic acid was allowed to react at 35° C. for 110 hours so as to measure the concentrations of the substrates and products contained in the reaction mixture. FIG. 1 shows the results.

An additional experiment was carried out similarly, except that the uracil-thymine decomposing enzyme solution was not added to the reaction solution, so as to measure the concentrations of the substrates and the products contained in the reaction mixture. Table 2 shows the results.

Figure 2:
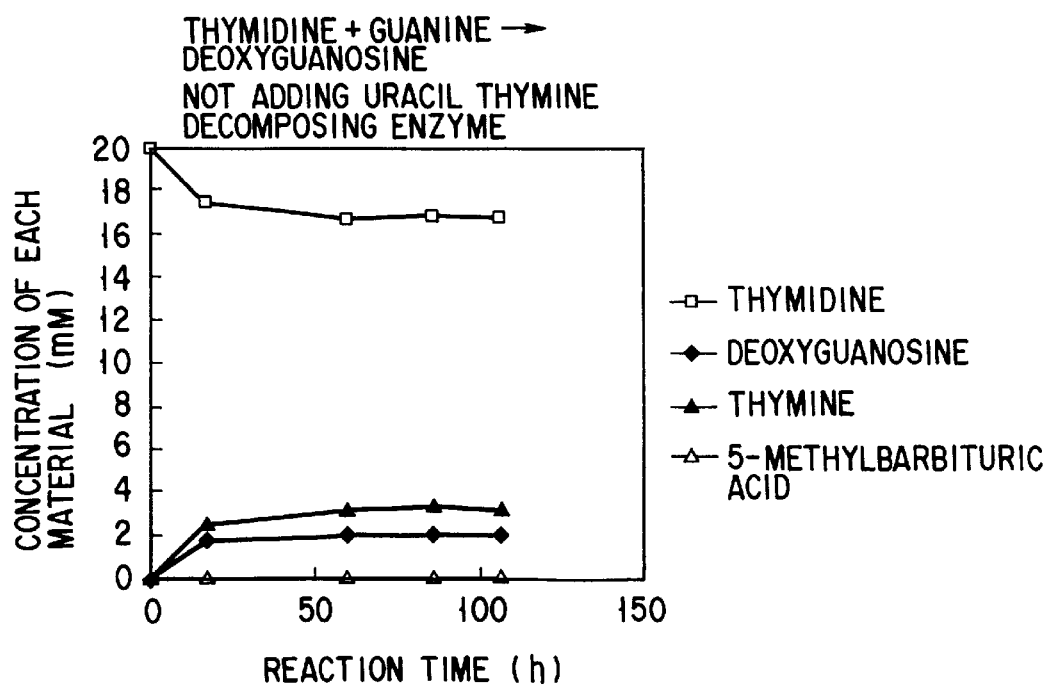
FIG. 2 is a graph showing changes with time in the concentration of each of the components of the reaction system in Example 1, which did not contain an uracil thymine decomposing enzyme solution.

In each of FIGS. 1 and 2, thymidine is denoted by white squares, and deoxyguanosine is denoted by black diamonds. Further, thymine and 5-methyl barbituric acid are denoted by black triangles and white triangles, respectively.

FIG. 1 shows formation of 5-methyl barbituric acid. Since the acid is decomposed so as to disappear, it has been clarified that uracil thymine dehydrogenase and barbiturase are present in the uracil-thymine decomposing enzyme. In the case of FIG. 1, thymidine disappeared substantially completely, though the starting material guanine was found to remain only slightly. Deoxyguanosine was formed in an amount of 14.9 mM (yield of 75%). Compared with FIG. 2 covering the case where uracil-thymine decomposing enzyme solution was not present, FIG. 1 supports that the desired product of deoxyguanosine was formed in a very large amount.

Examples 2 to 11
Preparation of Purine Nucleosides Using Various Starting Material Nucleosides and Various Starting Material Purine Bases Reaction was carried out at 35+ (for 90 hours under the same conditions as in Example 1, except that used were pyrimidine nucleoside compounds and purine bases shown in Table 3. The concentrations of the substrates and products contained in the reaction mixture were measured, with the results as shown in Table 3. Table 3 also shows comparative examples. These comparative examples were same as the Examples, except that 0.5 mL of distilled water was added to the reaction system in place of the uracil-thymine decomposing enzyme solution used in the Examples. As apparent from Table 3, the yield of purine nucleoside compound is increased by the addition of uracil-thymine decomposing enzyme solution. Particularly, the yields of guanosine and deoxyguanosine were markedly increased by the addition of uracil·thymine decomposing enzyme solution.

stabilizer were used.), 0.02 mL of PUNP·PYNP enzyme solution prepared in Preparation Example 1, and 0.01 mL of

TABLE 3

| | Raw materials | | | Formed amount (mM) Uracil.thymine decomposing enzyme | |
|---|---|---|---|---|---|
| Ex. | Pyrimidine nucleoside compound | Purine base | Formed purine nucleoside compound | Pre-sent | Ab-sent |
| 2 | Thymidine | Adenine | Deoxyadenosine | 17.7 | 8.8 |
| 3 | Thymidine | Hypoxanthine | Deoxyinosine | 16.4 | 12.4 |
| 4 | Thymidine | Benzimidazole | Benzimidazole deoxyriboside | 17.7 | 15.7 |
| 5 | Deoxy-uridine | Adenine | Deoxyadenosine | 16.6 | 8.8 |
| 6 | Deoxy-uridine | Adenine | Deoxyguanosine | 15.4 | 2.2 |
| 7 | Deoxy-uridine | Hypoxan-thine | Deoxyinosine | 15.9 | 11.7 |
| 8 | Deoxy-uridine | Benz-imidazole | Benzimidazole deoxyriboside | 17.2 | 13.9 |
| 9 | Uridine | Adenine | Adenosine | 12.9 | 3.7 |
| 10 | Uridine | Guanine | Guanosine | 13.4 | 2.2 |
| 11 | Uridine | Hypoxan-thine | Inosine | 16.2 | 11.2 |

Example 12
Effect of Uracil·Thymine Decomposing Enzyme Solution Derived from Any of the Strains on Formation of Purine Nucleoside Compound Prepared was 100 mL of a solution (pH 7) containing 20 mM of thymidine, 20 mM of guanine, 1.25 mM of potassium phosphate, 2 mL of PUNP·PYNP enzyme solution prepared in Preparation Example 1, 0.5 mL of uracil·thymine decomposing enzyme solution derived from any of the strains, which was prepared in Preparation Example 2, 100 mM of boric acid and 4 mM of ethylenediaminetetraacetic acid. In this example, comparative examples were also carried out in a same way except that 0.5 mL of distilled water was added to the reaction system in place of the uracil·thymine decomposing enzyme solution used.

The reaction system was subjected to reaction at 35° C. for 100 hours so as to measure the concentrations of the substrates and products contained in the reaction mixture. Table 4 shows the results.

The uracil·thymine decomposing enzyme solution derived from any of the strains was found to be effective for improving the yield of the product deoxyguanosine.

TABLE 4

| | Deoxyguanosine formation (mM) Uracil · thymine decomposing enzyme solution | |
|---|---|---|
| Strain | Present | Absent |
| Arthrobacter species YGK 222 | 12.4 | 2.4 |
| Bacillus megaterium YGK 252 | 3.2 | 2.4 |
| Pseudomonas species YGK 443 | 2.7 | 2.4 |
| Rhodococcus erythropolis JCM 3132 | 5.3 | 2.4 |
| Rhodococcus erythropolis JCM 3191 | 4.6 | 2.4 |

Example 13
Stabilization of intermediate product (ribose 1-phosphate) and inhibition of decomposition by phosphatase One milliliter (mL) of an aqueous solution (pH 7) containing 5 mM of ribose 1-phosphate, the stabilizer shown in Table 5 (4 mM of EDTA and 100 mM of each of other stabilizer were used.), 0.02 mL of PUNP·PYNP enzyme solution prepared in Preparation Example 1, and 0.01 mL of uracil·thymine decomposing enzyme solution derived from Arthrobacter species YGK 222, which was prepared in Preparation Example 2, was subjected to reaction at 35° C. for 72 hours. The presence of ribose 1-phosphate and ribose resulting from decomposition of ribose 1-phosphate in the reaction mixture was examined by a thin layer chromatography, the results being shown in Table 5. The examination was performed by a method described by Ishii et al. in "Agric. Biol. Chem., 53(12), 3209–3218 (1989)", which is incorporated herein by reference. Table 5 also shows a control, which was carried out in a same way except that 100 mL of tris(hyroxymethyl)aminomethane hydrochloride (hereinafter referred to as "tris") was added to the reaction system in place of the PUNP·PYNP enzyme solution and uracil·thymine decomposing enzyme solution used. Incidentally, the symbol "+" shown in Table 5 denotes that decomposition of ribose 1-phosphate was observed, with the symbol "−" denoting that the decomposition was not observed.

In the control, i.e., "tris(control)", in which enzyme solution was not added, the decomposition did not much proceed, supporting that phosphatase was contained in the enzyme solution. On the other hand, decomposition of ribose 1-phosphate was not observed in the case of using both boric acid and EDTA, supporting that these stabilizers serve to inhibit the activity of phosphatase contained in the enzyme solution and contribute to stabilization of ribose 1-phosphate.

TABLE 5

| Stabilizer | Decomposition of ribose 1-phosphate |
|---|---|
| Tris (control) | + |
| Tris | + |
| Boric acid | ± |
| Glycine | ± |
| Boric acid + glycine | ± |
| Boric acid + tris | ± |
| Tris + EDTA | + |
| Boric acid + EDTA | − |
| Glycine + EDTA | ± |
| EDTA | + |

Example 14
Effect of Stabilizer in Deoxyguanosine Formation 100 mL of an aqueous solution (pH 7) containing 20 mM of thymidine, 20 mM of guanine, the stabilizer shown in Table 6, 2 mL of PUNP·PYNP enzyme solution prepared in Preparation Example 1, and 0.5 mL of uracil·thymine decomposing enzyme solution derived from Arthrobactor species YGK 222, which was prepared in Preparation Example 2, was subjected to reaction at 35° C. for 90 hours. The amount of the stabilizer marked with "*" in Table 6 was 4 mM, the amount of the other stabilizer being 100 mM. The amount of deoxyguanosine contained in the reaction mixture was measured, the results being shown in Table 6.

The experimental data support that the combination of boric acid and a complex-forming compound similar to EDTA, said combination being also tested in Example 13, is effective for inhibiting decomposition of ribose 1-phosphate so as to stabilize ribose 1-phosphate and, thus, to improve the efficiency of forming a purine nucleoside compound.

TABLE 6

| Stabilizer | Deoxyguanosine formation (mM) |
|---|---|
| Tris (control) | 0 |
| Boric acid | 1.5 |
| Glycine | 0 |
| Iminodiacetic acid* | 0 |
| Nitrilotriacetic acid* | 0 |
| EDTA* | 0 |
| EGTA* | 0 |
| Tris + EDTA* | 0 |
| Glycine + EDTA* | 0.4 |
| Boric acid + tris | 2.0 |
| Boric acid + glycine | 4.7 |
| Boric acid + iminodiacetic acid* | 4.9 |
| Boric acid + nitrilotriacetic acid* | 11.6 |
| Boric acid + EDTA* | 12.7 |
| Boric acid + EGTA* | 9.6 |

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A method of preparing a purine nucleoside compound, comprising the step of subjecting a pyrimidine nucleoside compound and a purine base to a base exchange reaction in an aqueous solution containing phosphate ions in the presence of purine nucleoside phosphorylase and pyrimidine nucleoside phosphorylase, wherein pyrimidine base formed by the reaction is converted by a microorganism or an enzyme derived from the microorganism into a compound incapable of acting as substrates of pyrimidine nucleoside phosphorylase and purine nucleoside phosphorylase, wherein said microorganism is selected from the group consisting of genus Arthrobactor, genus Bacillus, genus Pseudomonas and genus Rhodococcus.

2. The method of preparing a purine nucleoside compound according to claim 1, wherein at least one compound selected from the group consisting of glycine, iminodiacetic acid, nitrilotriacetic acid, ethylenediaminetetraacetic acid and ethylene glycol (2-aminoethyl ether) tetraacetic acid, and boric acid or a borate are added as a stabilizer of ribose 1-phosphate or deoxyribose 1-phosphate which is formed as an intermediate in the base exchange reaction.

3. The method of preparing a purine nucleoside compound according to claim 1 or 2, wherein said pyrimidine nucleoside compound is a compound selected from the group consisting of uridine, deoxyuridine, 5-methyl uridine and thymidine.

4. The method of preparing a purine nucleoside compound according to claim 1 or 2, wherein said purine base is a compound selected from the group consisting of adenine, guanine, benzimidazole, halogenated purine and aminated purine.

5. The method of preparing a purine nucleoside compound according to claim 1 or 2, wherein said enzyme derived from microorganism is uracil thymine dehydrogenase or dihydrouracil dehydrogenase.

6. The method of preparing a purine nucleoside compound according to claim 1, wherein said microorganism is Arthrobactor species YGK 222 (FERM BP-5907), *Bacillus megaterium* YGK 252 (FERM BP-5908), Pseudomonas species YGK 443 (FERM BP-5909), *Rhodococcus erythropolis* JCM 3132 or *Rhodococcus erythropolis* JCM 3191.

* * * * *